(12) United States Patent
Lee et al.

(10) Patent No.: US 9,107,611 B2
(45) Date of Patent: Aug. 18, 2015

(54) OPTICAL COHERENCE TOMOGRAPHY DEVICE CAPABLE OF CONTROLLING MEASURING POSITION

(71) Applicant: HUVITZ CO., LTD., Gyeonggi-Do (KR)

(72) Inventors: Weon-Joon Lee, Gyeonggi-Do (KR); Joong-Jae Lee, Gyeonggi-Do (KR)

(73) Assignee: HUVITZ CO., LTD., Gyeonggi-Do (KR)

( * ) Notice: Subject to any disclaimer, the term of this patent is extended or adjusted under 35 U.S.C. 154(b) by 0 days.

(21) Appl. No.: 14/198,699

(22) Filed: Mar. 6, 2014

(65) Prior Publication Data

US 2014/0253926 A1    Sep. 11, 2014

(51) Int. Cl.
*G01B 9/02* (2006.01)
*A61B 3/10* (2006.01)

(52) U.S. Cl.
CPC ...................... *A61B 3/102* (2013.01)

(58) Field of Classification Search
CPC ...... G01B 9/02; A61B 5/0066; A61B 5/6852; A61B 5/0073; G01N 21/4795
USPC ........................................ 356/479
See application file for complete search history.

(56) References Cited

U.S. PATENT DOCUMENTS

2007/0188707 A1\* 8/2007 Nanjo ........................ 351/206
2012/0188508 A1\* 7/2012 Kim et al. ................... 351/206

\* cited by examiner

*Primary Examiner* — Tarifur Chowdhury
*Assistant Examiner* — Md Rahman
(74) *Attorney, Agent, or Firm* — Nath, Goldberg & Meyer; Jerald L. Meyer; Leonid D. Thenor (57) ABSTRACT

An optical coherence tomography device (OCT) is capable of controlling a distance between an eye to be examined (object) and the OCT and accurately center-aligning the eye. A mire ring optical system emits a measuring mire ring light to an object to be examined. A dichroic mirror separates an optical path of illumination light reflected from the object from the optical path of the signal light originating from the tomographic image formation section and delivers a reflected image to an image formation section and a tomographic image formation section. An objective lens condenses light reflected from the object, and a controller calculates movement distance of the OCT from the difference between a position of the image of the mire ring light and a position of an optical axis of the OCT The OCT is then moved according to the calculated movement.

6 Claims, 4 Drawing Sheets

OPTICAL COHERENCE TOMOGRAPHY DEVICE CAPABLE OF CONTROLLING MEASURING POSITION

This application claims the priority benefit of Korean Patent Application No. 10-2013-0024934 filed on Mar. 8, 2013. All disclosure of the Korean Patent application is incorporated herein by reference.

BACKGROUND OF THE INVENTION

1. Field of the Invention

The present invention relates to an optical coherence tomography device capable of controlling measuring position, and more particularly, to an optical coherence tomography device which is capable of controlling a working distance between an eye (an object to be examined) and the optical coherence tomography device and capable of accurately center-aligning the eye with the optical coherence tomography device.

2. Background Art

It is necessary to non-invasively obtain photographs of 2-dimensional tomographic (sliced) images of patient's eye for an ophthalmological operation such as a cornea operation or a cataract operation etc. For this, there has been used an optical coherence tomographic apparatus (optical coherence tomography: OCT) by which tomographic images of bio-tissue can be obtained with high resolution of submicrometers.

Figure 1:
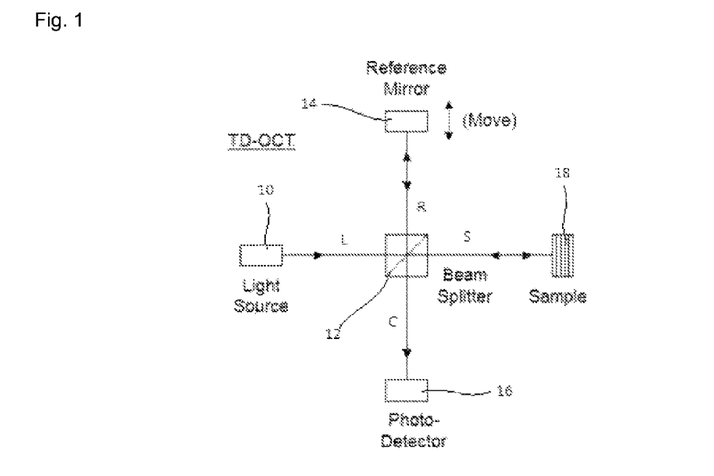
FIG. 1 illustrates a block diagram of a tomographic image formation section used in a conventional time domain (TD)-optical coherence tomography (OCT) (TD-OCT)

FIG. 1 shows a block diagram of a tomographic image formation section used in a conventional time domain-optical coherence tomography device (TD-OCT). As shown in FIG. 1, the tomographic image formation section of the TD-OCT has a light source (10), a beam splitter (12), a reference mirror (14) and a photo detector (16). The light source (10) emits a broadband low-coherence light (L) having short coherence length and the beam splitter (12) is for splitting the broadband low-coherence light (L) into a reference light (R) and a signal light (S). The reference mirror (14) moves along the propagation direction of the reference light (R) and reflects the reference light (R). The photo detector (16) detects an interference light (C) which is a superimposed light of the signal light (S) reflected from a specific depth of the sample (18) to be examined (for example, eyeball) and the reference light (R) reflected from the reference mirror (14).

Figure 2:
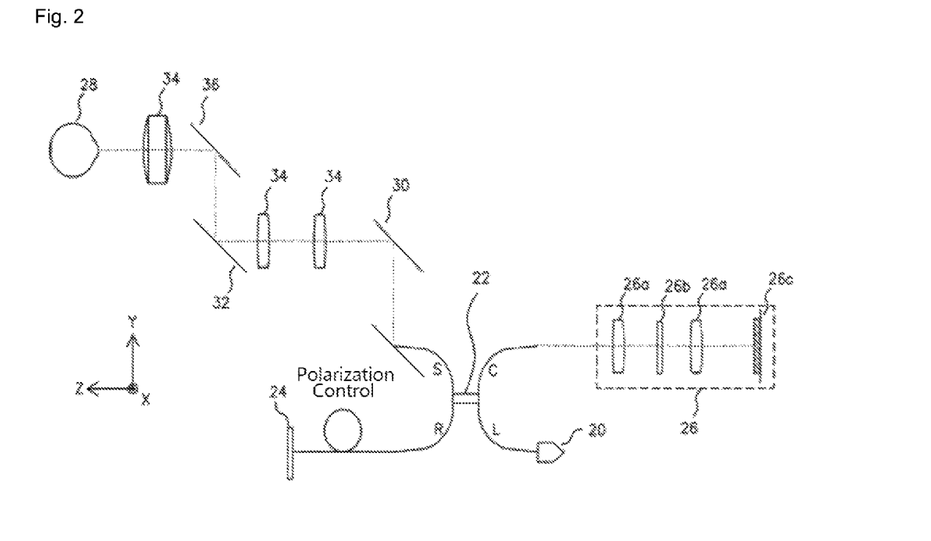
FIG. 2 illustrates a block diagram of a tomographic image formation section used in another conventional device of spectral domain (SD)-OCT (SD-OCT)

FIG. 2 shows a block diagram of a tomographic image formation section used in another conventional device of spectral domain-optical coherence tomography (SD-OCT). As shown in FIG. 2, the tomographic image formation section of the SD-OCT has a light source (20), a fiber coupler (22), a reference mirror (24) and a photo detector (26). The light source (20) emits a broadband low-coherence light (L) having short coherence length and the fiber coupler (22) divides the broadband low-coherence light (L) into a reference light (R) and a signal light (S). The reference mirror (24) is located fixedly along the propagation direction of the reference light (R) and reflects the reference light (R). The photo detector (26) detects an interference light (C) which is the superimposed light of the signal light (S) reflected from a specific depth of the object to be examined (28) and the reference light (R) reflected from the reference mirror (24). The photo detector (26) has a collimator lens (26a) for collimating the interference light (C), a diffraction grating (26b) for spectrally dividing the interference light (C), a line scan camera (26c) for detecting the spectrally divided interference light (C) and so on. Further, optionally, on the optical path of the signal light (S) are provided a X-scanner (32) and a Y-scanner (30) for moving a target position of the signal light (S) in X-direction and Y-direction respectively on XY-plane, a collimator lens (34) for collimating the signal light (S), and a reflection mirror (36) for changing the optical path of the signal light (S), and so on. The X-scanner (32) and the Y-scanner (30) is for obtaining 2-dimensional or 3-dimensional tomographic images of the object to be examined (28) and may a galvano mirror for scanning the signal in X-direction and Y-direction respectively. With the broadband light source (20), the fixed reference mirror (24), the diffraction grating (26b) and the line scan camera (26c) of the SD-OCT in FIG. 2, tomographic images of bio-tissue can be obtained with high resolution of submicrometers.

The above-mentioned OCTs have been used in a various biomedical fields, such as in obtaining tomographic images of eye (specifically, eyeball), skin endothelial structure, blood flow, teeth, gastro-intestinal tract and so on. When the OCT is used for obtaining tomographic images of eye, before measuring, by adjusting a working distance between the eye to be examined and the OCT, the signal light should be focused and also a center of eye, that is, a center of cornea should be center-aligned with a center of the OCT. In scanning retina by using the OCT, the scanning light of the OCT stops (namely, located) on a pupil of the eye. That is, the scanning lights of all directions are collected in one point of the pupil and then spread out over every parts of the retina. Here, the working distance between the eye to be examined and the OCT should be exactly adjusted. Otherwise, the stop position of the scanning light varies (that is, the scanning light does not located at the pupil center) so that there is generated a vignetting effect which causes a signal loss in obtaining the retina images. For eliminating such vignetting effect, the working distance and the center-alignment should be accurately adjusted. Conventionally, an examiner has adjusted the working distance and aligned the center of the eye while observing the eyeball image with his or her naked eyes, which is dependent on the examiner's experience. Therefore, the conventional art has some drawbacks such that a measuring accuracy is insufficient and then it takes a long time to obtain the tomographic images of the eye.

SUMMARY OF THE INVENTION

Accordingly, it is an object of the present invention to provide an optical coherence tomography device which is capable of controlling a working distance between an eye of object to be examined and the optical coherence tomography device and capable of accurately center-aligning the eye with the optical coherence tomography device.

It is another object of the present invention to provide an optical coherence tomography device reducing a vignetting effect which causes a signal loss in obtaining the image signal.

It is still another object of the present invention to provide an optical coherence tomography device with which the tomographic images of the eye can be obtained in short time regardless of an examiner's skill, by automatically adjusting a working distance between an eye and the optical coherence tomography device and center-aligning the eye with the optical coherence tomography device.

To achieve the above objects, the present invention provides an optical coherence tomography device (OCT) comprising: a mire ring optical system for emitting a measuring mire ring light to an object to be examined; an image formation section for detecting an image of an illumination light reflected from the object and an image of the mire ring light reflected from the object; a tomographic image formation section for emitting a signal light to the object and obtaining a tomographic image of the object; a dichroic mirror for separating an optical path of the illumination light reflected from the object and the optical path of the signal light originating in the tomographic image formation section and for delivering a reflected image of the illumination light and a reflected image of the signal light to the image formation section and the tomographic image formation section, respectively; an objective lens for condensing the signal light and the illumination light which are incident to and reflected from the object; and a controller for calculating movement distance of the OCT in up-and-down directions and right-and-left directions, from the difference between a position of the image of the mire ring light and a position of an optical axis of the OCT, and then moving the OCT according to the calculated movement distance in up-and-down directions and right-and-left directions thereby making the position of the image of the mire ring light to be coincided with the position of the optical axis of the OCT.

As described above, by using the present optical coherence tomography device, automatic adjustment of a working distance between the eyeball of object to be examined and the optical coherence tomography and center-alignment of the eyeball with the optical coherence tomography can be made so that images of the eyeballs can be obtained in short time regardless of an examiner's skill.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

Reference will be now made in detail to the preferred embodiments of the present invention with reference to the attached drawings.

Figure 3:
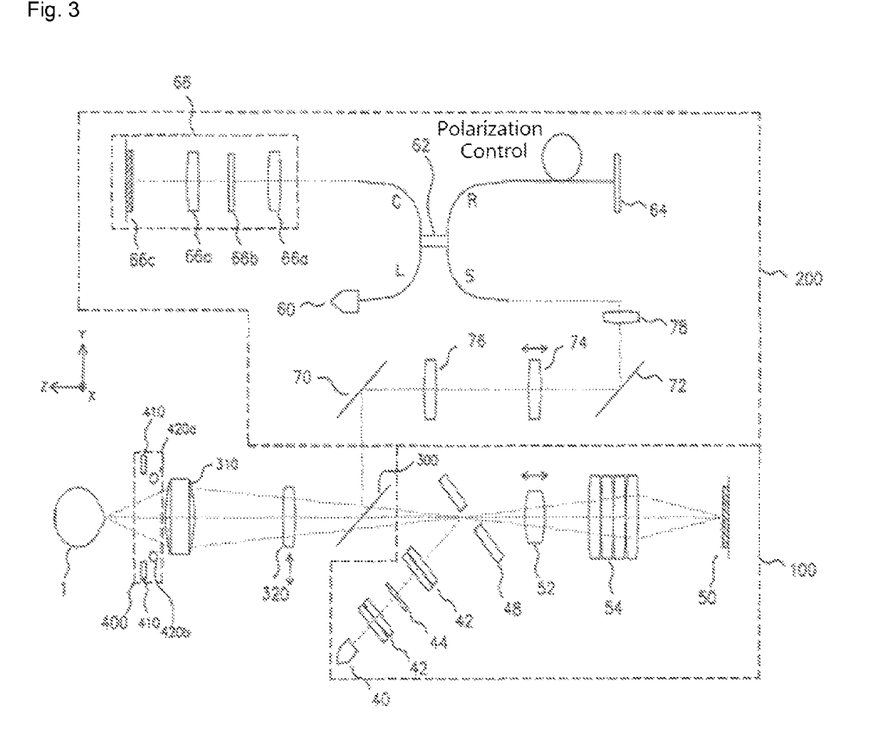
FIG. 3 illustrates a block diagram of an optical coherence tomography (OCT) according to one embodiment of the present invention.

FIG. 3 illustrates a block diagram of an optical coherence tomography (OCT) according to one embodiment of the present invention. As illustrated in FIG. 3, the OCT according to the present invention includes a mire ring optical system (400), an image formation section (100), a tomographic image formation section (200), a dichroic mirror (300), an objective lens (310), a controlling section (not shown), and optionally, a lens (320) for adjusting image-obtaining depth.

Figure 4:
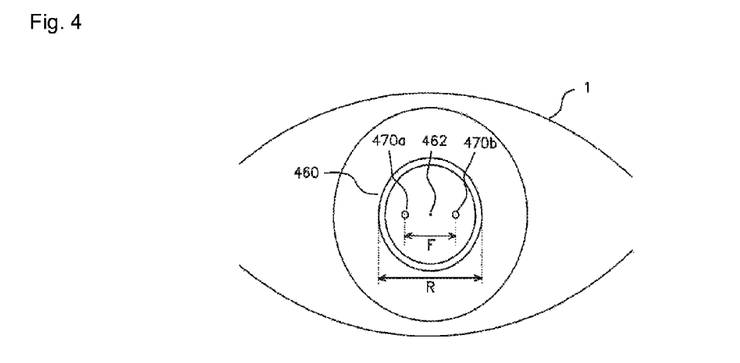
FIG. 4 illustrates images of a mire ring light and a focus light which are formed on cornea, the mire ring light and the focus light resulting from a mire ring optical system, in the OCT according to one embodiment of the present invention.
Figure 8:
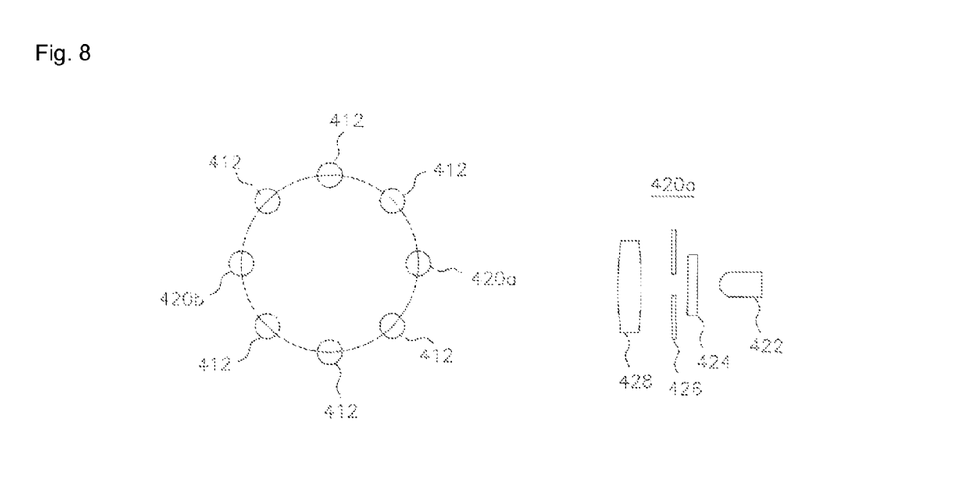
FIG. 8 illustrates an example of the mire ring optical system used in the OCT according to one embodiment of the present invention.

The mire ring optical system (400) includes a mire-ring light source (410) for generating a mire-ring measuring light emitted onto a cornea of the examinee's eye (1) and when needed, further includes focus light sources (420a, 420b) for generating focus light by which at least two focus images are formed on the cornea of the examinee's eye (1). The mire-ring light source (410) is for emitting a doughnut-shaped mire-ring measuring light which is focused on the cornea, and for example, as shown in FIG. 8, includes a plurality of light emitting diodes (LEDs, 412) which are arranged in a ring-shape, and a mire-ring (not shown) positioned in front of a plurality of LEDs (412) for converting the light of LEDs (412) into a mire-ring measuring light. The focus light sources (420a, 420b) are for emitting at least two focus lights parallel to the optical axis of the OCT, and for example, as shown in FIG. 8, includes a focus light source (422) and a diffuser (424) for emitting a diverging focus light, a pin hole (426) for converting the diverging focus light into a point-shaped focus light, and a collimation lens (428) for collimating the point-shaped focus light. That is, in the mire ring optical system (400) of FIG. 8, a plurality of LEDs (412) are arranged in a ring-shape on the surroundings of the objective lens (310) and a diffuser is provided before the LEDs (412), thereby forming a mire-ring light source (410) which is a finite light source. Meanwhile, the diffuser (424), the pin hole (426) and the collimation lens (428) are provided in front of the two LEDs (422) to form focus light sources (420a,420b) which are infinite light sources. Preferably, the two LEDs (422) are positioned symmetrically, namely, at the opposite sites. The size of the finite light is varied according to the variation of the working distance of the optical system. Meanwhile, the distance between the two infinite lights is maintained constantly even though the size of each infinite light is varied according to the variation of the working distance of the optical system. By using the features of the finite light and the infinite lights mentioned above, the working distance can be accurately controlled. The mire-ring light source (410) may be formed by variously arranging a plurality of LEDs in straight line, oval or rectangular shape as well as in ring shape. Also, the focus light sources (420a, 420b) may be positioned inside or outside of the mire-ring light source (410), or may be overlapped with the mire-ring light source (410). The focus light sources (420a, 420b) may be parallel lights consisting of a pair of point lights (470a, 470b) as shown in FIG. 4, parallel lights consisting of three point lights which are positioned as the shape of "T" or parallel lights consisting of three point lights each of which is arranged on a circle circumference apart from 120-degree. The image of the focus light may be normally formed in the center of the cornea of the examinee's eye (1), but in case of a patient having drooping eyelids, image of the focus light may be formed in the lower part rather than the center of the cornea of the examinee's eye (1).

FIG. 4 illustrates images from a mire ring light and focus lights which are formed on cornea, the mire ring light and the focus lights resulting from the mire ring optical system, in the OCT of the present invention. As shown in FIG. 4, the mire ring light emitted from the mire ring light source (410) is incident to the cornea on which ring-shaped image (460, the mire-ring-light image) is formed, and also the focus lights emitted from the focus light sources (420a, 420b) are incident to the cornea on which two point-shaped images (470a, 470b, the focus-light-images) are formed. The position of the mire-ring-light (460) is represented by a position of the center thereof, the size of the mire-ring-light (460) is represented by a diameter (R) thereof, and the size of the focus-light-images (470a, 470b) is represented by a distance (F) between two points thereof.

Returning to FIG. 3, the mire ring light and the focus lights are incident to the image formation section (100) in which images thereof are formed and detected. The image formation section (100) includes an image device (50) for detecting the mire-ring-light image (460) and the focus-light-images (470a, 470b) which are reflected from a cornea of the examinee's eye (1), and optionally, further includes condensing lenses (52, 54) for condensing and delivering the mire-ring-light image (460) and the focus-light-images (470a, 470b). The mire ring light emitted from the mire ring light source (410) and the focus lights emitted from the focus light sources (420a, 420b) are reflected from the cornea of the examinee's eye (1), condensed by the objective lens (310) and the lens (320) for adjusting image-obtaining depth, transmitted through a hole formed in a center of an aperture mirror (48), and optionally, are condensed by the condensing lens (52, 54), and thereafter the mire-ring-light image (460) and the focus-light-images (470a, 470b) are formed at the image device (50). As described below, because the lens (320) for adjusting image-obtaining depth makes the focal point of the optical system be on the cornea of the examinee's eye (1), not only cornea image but also the mire ring light source (410) and the focus light sources (420a, 420b) around the objective lens (310) can be clearly seen. In case of scanning a retina, the lens (320) for adjusting image-obtaining depth is removed so that the focal point of the optical system is on the retina.

Figure 5:
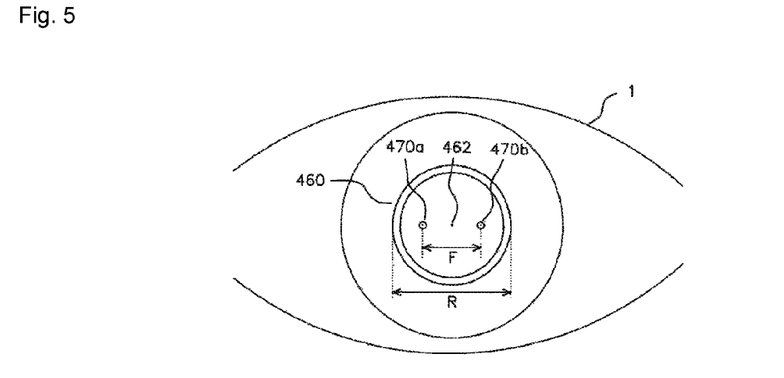
FIG. 5 illustrates a method of aligning a center of an examinee's cornea with an optical axis of the OCT, in the OCT according to one embodiment of the present invention.

For aligning the cornea center of the examinee's eye (1) with the optical axis of the OCT, a controller (not shown) installed in the OCT according to the present invention calculates movement of the OCT in up-and-down directions and right-and-left directions, from the difference between the position (center point) of the mire-ring light image (460) and the position of the optical axis of the OCT, and then moves the OCT according to the calculated movement. FIG. 5 illustrates a method of aligning a center of an examinee's cornea with an optical axis of the OCT, in the OCT according to one embodiment of the present invention. As shown in FIG. 5, the optical axis of the OCT is located in a center point (O) of the image (580) formed at the image formation section (100), and the center point (462) of the mire-ring-light image (460) formed on the cornea is located in a center point of the cornea of the examinee's eye (1). The displacement error ($\Delta X$) in X-axis direction (right-and-left direction) and the displacement error ($\Delta Y$) in Y-axis direction (up-and-down direction), for moving from the center point (O) of the image (580) to the center point (462) of the mire-ring-light image (460), are calculated. The OCT is moved by the calculated displacement error ($\Delta X$, $\Delta Y$) in X-axis and Y-axis directions so that the center of the cornea is aligned with the optical axis of the OCT. Since the mire-ring-light image (460) serves as the vivid signal light capable of figuring out the position of the cornea, the above-mentioned method is more accurate than a conventional method using the image of eyeball in the position adjustment of the optical system. When the center point (462) of the mire-ring-light image (460) does not coincide with a center of the examinee's pupil, when needed, the centering between the OCT and the eye (1) may be carried out so that the center point (462) is aligned with the center of the examinee's pupil instead of the center point (O) of the image (580) formed at the image formation section (100).

Figure 6:
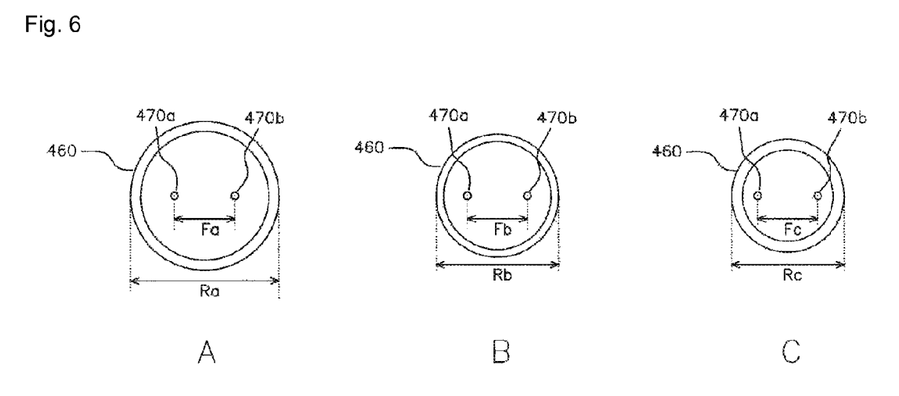
FIG. 6 illustrates a relation between an examinee's eyeball position and the images of the mire ring light and the focus light, in the OCT according to one embodiment of the present invention.

Next, the method for locating the cornea of the examinee's eye (1) at a focal point of the measuring light will be explained, which is accomplished by calculating a back-and-forth displacement of the OCT based on the size (R) of the mire-ring-light image (460) and the size (F) of the focus-light images (470a, 470b), and them moving the OCT by the calculated amount. FIG. 6 illustrates a relation between the mire-ring-light image (460) and the focus-light images (470a, 470b) in case where the examinee's eye (1) is inside of the focal point of the measuring light (A), the examinee's eye (1) is at the focal point of the measuring light (B), and the examinee's eye (1) is beyond the focal point of the measuring light (C). As shown in FIG. 6(B), the mire ring light is a finite light source, so when the examinee's eye (1) is at the focal point of the optical system of the OCT, the mire-ring-light image (460) is most vivid on the cornea of the examinee's eye (1) and there is no blurring around the mire ring light. As shown in FIG. 6(A), when the examinee's eye (1) is inside of the focal point of the optical system of the OCT, being toward the OCT, the diameter (Ra) of the mire-ring-light image (460) is increased. As shown in FIG. 6(C), when the examinee's eye (1) is beyond the focal point of the optical system of the OCT, being away from the OCT, the diameter (Rc) of the mire-ring-light image (460) is decreased. On the other hand, the focus lights are infinitely distance light source and parallel to each other, so the focus-light images (470a, 470b) are formed on a constant site of the cornea and each distance (Fa, Fb, Fc) between the focus lights is all same regardless of the position of the examinee's eye (1). Accordingly, the controller (not shown) of the OCT determines whether or not the examinee's eye (1) is on the focal point of the optical system of the OCT, and then moves the OCT in forward and backward directions based on the determination result until the examinee's eye (1) is on the focal point of the optical system of the OCT.

Another example for calculating the movement of the OCT in back-and-forth direction is as follows. A focus distance (D, $D=R-F$) is defined as a difference between the diameter (R) of the mire-ring light image (460) and the size (F) of the focus-light images (470a, 470b). When the examinee's eye (1) is at the focal point of the optical system of the OCT (FIG. 6(B)), the focus distance (Db) is Rb−Fb. When the examinee's eye (1) is inside of the focal point of the optical system of the OCT (FIG. 6(A)), the focus distance (Da) is Ra−Fa and then Da>Db. On the other hand, when the examinee's eye (1) is beyond the focal point of the optical system of the OCT (FIG. 6(C)), the focus distance (Dc) is Rc−Fc and then Dc<Db. First, the controller (not shown) of the OCT measures a standard focus distance (Db) which is determined when the examinee's eye (1) is at the focal point of the optical system of the OCT. Then, after measuring the focus distance (D) of the examinee's eye (1), the controller determines whether or not a difference (D−Db) between the measured focus distance (D) and the standard focus distance (Db) is in a predetermined range (for example 0.2 to 0.4 mm), and, then when it is turned out that the difference (D−Db) is out of the range, the controller adjusts the back-and-forth position of the OCT until the difference (D−Db) is within the range. For instance, when the difference (D−Db) is more than 0.4 mm, the controller determines that the examinee's eye (1) is inside of the focal point of the optical system of the OCT and then moves the OCT backwardly (away from the eye (1)), while when the difference (D−Db) is less than 0.2 mm, the controller determines that the examinee's eye (1) is beyond the focal point of the optical system of the OCT and then moves the OCT forwardly (toward the eyeball (1)), whereby the examinee's eye (1) is at the focal point of the optical system of the OCT.

Still another example for calculating the movement of the OCT in back-and-forth direction uses a ratio of D to Db (D/Db). When D/Db is more than 2, the controller (not shown) in the OCT considers that the examinee's eye (1) is inside of the focal point of the optical system of the OCT and then moves the OCT backwardly, and when D/Db is less than 1.2, the controller (not shown) in the OCT considers that the examinee's eye (1) is beyond the focal point of the optical system of the OCT and then moves the OCT forwardly. So, the examinee's eye (1) is at the focal point of the optical system of the OCT. Here, if necessary, the range of the difference (D−Db) and the ratio of D to Db (D/Db) can be correctly regulated according to a cornea curvature of the eye (1).

Still another method for locating the cornea of the examinee's eye (1) at the focal point of the optical system of the OCT uses an overlapping of the mire-ring-light image (460) with the focus-light images (470a, 470b). In a standard status, the mire ring light source (410) and the focus light sources (420a, 420b) of the mire ring optical system (400) are arranged so as for the mire-ring-light image (460) to be overlapped with the focus-light images (470a, 470b) when the eye (1) is at the focal point of the optical system of the OCT. In examining the eyeball (1), the controller moves the OCT backwardly or forwardly until the mire-ring-light image (460) is overlapped with the focus-light images (470a, 470b) so that the examinee's eye (1) is at the focal point of the optical system of the OCT.

In some cases, the focus light images (470a, 470b) are not used, and instead, the OCT is designed for the controller to determine that the examinee's eye (1) is at the focal point of the optical system of the OCT when the ring thickness in the mire-ring-light image (460) is minimum (that is, when the mire-ring-light image is most vivid). In examining the eye (1), the controller moves the OCT backwardly or forwardly until the ring thickness in the mire-ring-light image (460) is minimum so that the examinee's eye (1) is at the focal length of the optical system of the OCT.

Returning to FIG. 3, the image formation section (100) includes an illumination light source (40) for emitting an illumination light to the object (1, for example the eyeball) and the image device (50) (for example, a camera) for detecting image of the illumination light reflected from the object (1). On an optical path of the illumination light may be arranged at least one condensing lenses (42) for condensing the illumination light and further may be arranged a plate (44) which has a small black dot stamped in a center thereof. When the illumination light is reflected from a center of the objective lens (310), the reflected illumination light is incident to the image device (50), being a noise. So, for suppressing noise from the reflected illumination light, the black dot is stamped at a conjugate position of the plate (44) in relation with the center of the objective lens (310). The illumination light emitted from the illumination light source (40) is condensed by the condensing lenses (42), transmits through the plate (44) having the black dot stamped to be transformed into a donut-shaped light, then is reflected from a rim of an aperture mirror (48) which has a hole provided in a center thereof and finally illuminates the object (1). The image (image of the examinee's eyeball) of the reflected light, that is the illumination light reflected from the object (1), is condensed by the objective lens (310), transmits through the hole formed in the center of the aperture mirror (48), and if needed, condensed by the condensing lens (52) and the CCD lens (54) and then is delivered to the image device (50).

The tomographic image formation section (200) is a mean for emitting signal light (S) to the object of the examinee's eye (1) and then obtain a tomographic image of the eye (1). As the tomographic image formation section (200), a conventional tomographic image formation section shown in FIG. 1 and FIG. 2 can be used without limitation. In the OCT of FIG. 3, the tomographic image formation section of the SD-OCT in FIG. 2 is used. The tomographic image formation section (200) of FIG. 3 includes a light source (60), a fiber coupler (62), a reference mirror (64) and a photo detector (66). The light source (60) emits light (L) for taking a tomography and the fiber coupler (62) divides the light (L) into a reference light (R) and a signal light (S). The reference mirror (64) is located fixedly along the propagation direction of the reference light (R) and reflects the reference light (R). The photo detector (66) detects an interference light (C) which is the superimposed light by the signal light (S) reflected from a specific depth of the object (1) and the reference light (R) reflected from the reference mirror (64). The photo detector (66) has a condensing lens (66a) for condensing the interference light (C), a diffraction grating (66b) for spectrally dividing the interference light (C), a line scan camera (66c) for detecting the interference light (C) spectrum-divided and so on. Further, when needed, on the optical path of the signal light (S) are mounted a X-scanner (72) and a Y-scanner (70) for moving a target position of the signal light (S) in X-direction and Y-direction respectively on XY-plane, a collimator lens (74, 76, 78) for collimating the signal light (S), and so on.

In the tomographic image formation section (200), the light (L) for taking a tomography which is emitted from the light source (60) is divided at the fiber coupler (62) into the reference light (R) and the signal light (S) in any ratio, for example the ratio of 5:5 or 8:2. The reference light (R) is incident to the reference mirror (64) and then reflected therefrom, and the signal light (S) is incident to the object (1) such as a retina and then reflected therefrom. The reflected reference light (R) and the signal light (S) are superimposed to form the interference light (C). The interference light (C) is condensed by the condensing lens (66a) to be parallel, and then transmits through the diffraction grating (66b) to be spectrally divided. The spectrally divided light is again condensed by the condensing lens (66a), is delivered to the line scan camera (66c) to produce an interference signal with focusing. The analysis of the produced interference signal leads to generating tomographic images of the retina in a specific depth thereof. Scanning the retina in a specific depth or at a specific area thereof by adjusting the X-scanner (72) and the Y-scanner (70) results in obtaining the tomographic images of the retina. In such a tomography of the retina, the position of the focal point of the signal light (S) can be varied according to a refractive power of the eye (1). Thus, the condensing lens (74) is made to be moved backward or forward for searching the accurate position of the focal point of the signal light (S). The condensing lens (74) of the tomographic image formation section (200) and the condensing lens (52) of the image formation section (100) are both for compensating the position of the focal point of the signal light (S) according to the refractive power of the eye (1), so, they are fixed at a reference position in taking an image of the cornea while they are moved in taking an image of the retina along the refractive power of the eyeball. Therefore it is preferable to synchronize the condensing lens (74) and the condensing lens (52) and move the both simultaneously.

At the dichroic mirror (300), the optical path of the illumination light which originates in the image formation section (100) and is reflected from the object (1), and the optical path of the signal light (S) which originates in the tomographic image formation section (200) and is reflected from the object (1) are separated, so that the reflected image of the illumination light and the reflected image of the signal light (S) are delivered to the image formation section (100) and the tomographic image formation section (200), respectively. That is, at an intersection between the image formation section (100) and the tomographic image formation section (200) is positioned the dichroic mirror (300) serving as a spectrometer. The objective lens (310) condenses the signal light (S) and the illumination light (reflected) which are incident to or reflected from the object (1).

As shown in FIG. 3, the OCT of the present invention further includes the lens (320) for adjusting image-obtaining depth. The lens (320) may be inserted into or deviated (removed) from a common path of the illumination light of the image formation section (100) and the signal light (S) of the tomographic image formation section (200). The focal length of the illumination light and the signal light (S) are varied according to the insertion or deviation of the lens (320), so the tomographic images of the object apart from a given distance can be selectively taken by adjusting the position of the lens (320). In detail, in case when the lens (320) is inserted on a common path of the illumination light and the signal light (S) between the dichroic mirror (300) and the objective lens (310), the focus of the OCT is formed on the cornea so that the cornea image and tomographic images of the cornea can be obtained, wherein the lens (320) serves as the lens for the cornea photographing. That is, when the lens (320) is included in the optical system of the OCT, the OCT takes the tomography of the cornea. In this time, when the X-scanner (72) and the Y-scanner (70) are adjusted to scan the cornea in a specific depth or at a specific area thereof, the tomographic images of the cornea in a specific depth or at a specific area thereof can be obtained. Also, it is preferable that the lens (320) is positioned between the dichroic (300) which is the intersection of the paths of the illumination light and the signal light (S) and the objective lens (310). When the lens (320) is located in such a position, the influence of the lens (320) on the optical systems of the image formation section (100) and the tomographic image formation section (200) is minimum, so the optical system of the OCT can be designed simple and efficiently. If the lens (320) is located between the objective lens (310) and the object (1) or after the dichroic (300), the objective lens (310) or the object (1) can be destroyed by the lens (320), or the optical and mechanical construction for installing the lens (320) in the OCT can be complex.

Figure 7:
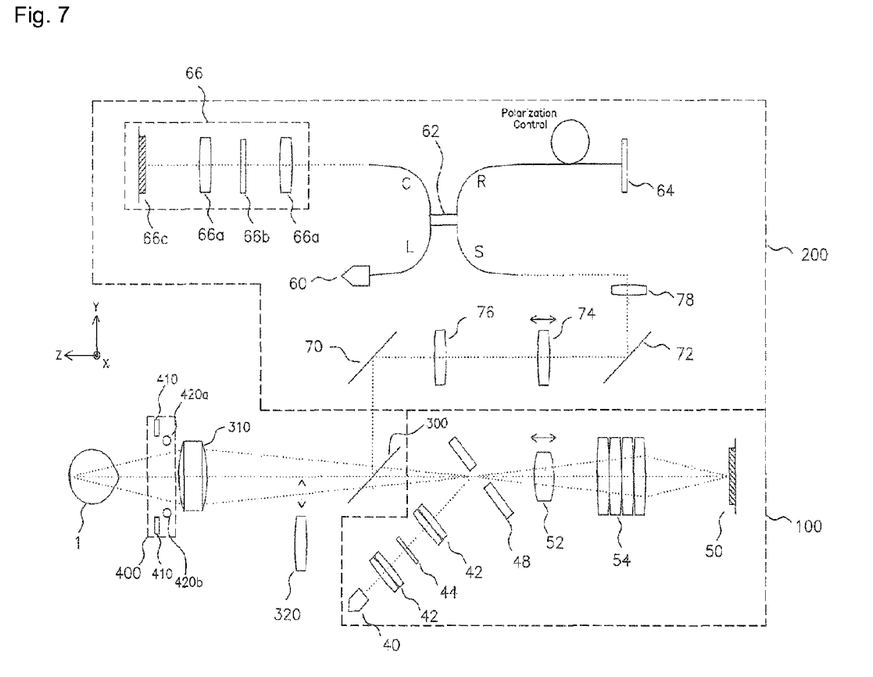
FIG. 7 illustrates a block diagram for obtaining a cornea image and tomographic images thereof in the OCT shown in FIG. 3.

On the other hand, as shown in FIG. 7, in case where the lens (320) is deviated from the optical paths of the illumination light and the signal light (S), the focus of the OCT is formed on the retina so that the retina image and the tomographic images of the retina can be obtained. That is, when the lens (320) is not included in the optical system of the OCT, the OCT takes the tomography of the retina. While when taking a photography of the retina image by using the image formation section (100) as shown in FIG. 7, the visibility of the retina image can be varied according to the refractive power of the eyeball. Thus, when the visibility thereof is low, the condensing lens (52) is forced to move forward and/or backward for enhancing the visibility of the retina image.

According to the method for obtaining the tomography of the cornea and the retina by using the OCT of the present invention, controlling a working distance between an eyeball of object to be examined and the optical coherence tomography, and center-aligning the eyeball with the optical coherence tomography can be done accurately and easily. In addition, when there is provided a guide program which processes with software the images formed in the image formation section (100) to find a position of the pupil and then aligns the OCT with the center of the pupil, the working distance and the center-aligning of the optical system can be automatically carried out. The OCT according to the present invention can be embedded in a medical system of ophthalmology operations such as the cornea operation, cataract operation and so on, or can be used as a separate medical instrument independently from the medical system of ophthalmology operations.

What is claimed is:

1. An optical coherence tomography device (OCT) comprising:
    a mire ring optical system for emitting a measuring mire ring light to an object to be examined;
    an image formation section for detecting an image of an illumination light reflected from the object and an image of the mire ring light reflected from the object;
    a tomographic image formation section for emitting a signal light to the object and obtaining a tomographic image of the object;
    a dichroic mirror for separating an optical path of the illumination light reflected from the object from the optical path of the signal light originating from the tomographic image formation section and delivering a reflected image of the illumination light and a reflected image of the signal light to the image formation section and the tomographic image formation section, respectively;
    an objective lens for condensing the signal light and the illumination light which are incident to and reflected from the object; and
    a controller for calculating movement distance of the OCT in up-and-down directions and right-and-left directions, from the difference between a position of the image of the mire ring light and a position of an optical axis of the OCT, and then moving the OCT according to the calculated movement distance in up-and-down directions and right-and-left directions thereby making the position of the image of the mire ring light to be coincided with the position of the optical axis of the OCT.

2. The optical coherence tomography device according to claim 1, wherein the mire ring optical system further comprises a focus light source for emitting at least two focus lights which are parallel to the optical axis of the OCT to the object, and
    from a diameter (R) of the image of the mire ring light which varies according to the position of the object and a size (F) of the image of the focus lights which are constant regardless of the position of the object, the controller determines whether the object is positioned on the focal point of the optical system of the OCT or not, and then moves the OCT in forward and backward directions so that the object is located at the focal point of the optical system of the OCT.

3. The optical coherence tomography device according to claim 2, wherein a focus distance (D) is a difference between the diameter (R) of the image of the mire ring light and the size (F) of the image of the focus lights, and
    the controller i) measures a standard focus distance (Db) which is a focus distance (D) when the object is at the focal point of the optical system of the OCT, ii) measures the focus distance (D) of the object at a certain measuring position, iii) determines whether a difference (D–Db) between the measured focus distance (D) and the standard focus distance (Db) is out of a predetermined range, and iv) moves the OCT in the in forward and backward directions so that the difference (D−Db) is in the predetermined value.

4. The optical coherence tomography device according to claim 2, wherein the mire ring light source and the focus light source of the mire ring optical system are positioned so that the image of the mire ring light and the images of the focus light are overlapped when the object is on the focal point of the optical system of the OCT, and the controller moves the OCT in forward and backward directions so that the object at a certain measuring position is on the focal point of the optical system of the OCT, and the image of the mire ring light and the images of the focus light are overlapped.

5. The optical coherence tomography device according to claim 2, further comprising a lens for adjusting image-obtaining depth which is inserted into or deviated from a common path of the illumination light of the image formation section and the signal light of the tomographic image formation section, and wherein the lens for adjusting image-obtaining depth changes the focal lengths of the illumination light and the signal light for selectively obtaining the tomographic images of the object at different positions.

6. An optical coherence tomography device (OCT) comprising:

a mire ring optical system for emitting a measuring mire ring light to an object to be examined;

an image formation section for detecting an image of an illumination light reflected from the object and an image of the mire ring light reflected from the object;

a tomographic image formation section for emitting a signal light to the object and obtaining a tomographic image of the object;

a dichroic mirror for separating an optical path of the illumination light reflected from the object from the optical path of the signal light originating from the tomographic image formation section and delivering a reflected image of the illumination light and a reflected image of the signal light to the image formation section and the tomographic image formation section, respectively;

an objective lens for condensing the signal light and the illumination light which are incident to and reflected from the object; and a controller for moving the OCT in forward and backward directions so that a ring thickness of image of the mire ring light become minimum and the object is located on the focal point of the optical system of the OCT.

* * * * *